United States Patent
Laguette

(10) Patent No.: US 6,638,305 B2
(45) Date of Patent: Oct. 28, 2003

(54) MONOFOCAL INTRAOCULAR LENS CONVERTIBLE TO MULTIFOCAL INTRAOCULAR LENS

(75) Inventor: Stephen W. Laguette, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/855,331

(22) Filed: May 15, 2001

(65) Prior Publication Data

US 2002/0188351 A1 Dec. 12, 2002

(51) Int. Cl.$^7$ .................................................. A61F 2/16
(52) U.S. Cl. ...................................... 623/6.37; 623/6.28
(58) Field of Search ............................... 623/4.1, 6.11, 623/6.2, 6.21, 6.22, 6.24, 6.27, 6.28, 6.29, 6.3, 6.37, 6.13, 6.19

(56) References Cited

U.S. PATENT DOCUMENTS

| | | | |
|---|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |

(List continued on next page.)

FOREIGN PATENT DOCUMENTS

| | | |
|---|---|---|
| AU | 3225789 | 10/1989 |
| DE | 2702117 | 7/1978 |
| DE | 3246306 | 6/1984 |
| EP | 0246216 | 11/1987 |
| EP | 0329981 | 8/1989 |

(List continued on next page.)

OTHER PUBLICATIONS

Video Tape "New Elliptical Acco. IOL for Cataract Surgery" Shown at ASCRS Symposium on Apr. 10, 1999 (Video Enclosed).
Partial Program Re: ASCRS Symposium, Showing Video Tape shown between Apr. 10–14, 1999.
Mandell, Contact Lens Practice, 4th Ed.
Holladay et al, J. Cataract Refractive Surg., vol. 14, 1/55. The Shah Bifocal Intraocular Lens Implant.

(List continued on next page.)

*Primary Examiner*—Corrine McDermott
*Assistant Examiner*—William H Matthews
(74) *Attorney, Agent, or Firm*—Frank J. Uxa; Peter Jon Gluck

(57) ABSTRACT

An intraocular lens for use in a mammalian eye includes an optic adapted to focus light toward a retina of the mammalian eye and, in cooperation with the mammalian eye, to provide accommodation, the optic being adapted to have a first configuration to provide substantially a single optical power and a second configuration to provide a plurality of different optical powers.

28 Claims, 3 Drawing Sheets

U.S. PATENT DOCUMENTS

| | | | |
|---|---|---|---|
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,435,856 A * | 3/1984 | L'Esperance ............... 351/57 |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,074,877 A | 12/1991 | Nordan |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,236,452 A | 8/1993 | Nordan |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,702,440 A | 12/1997 | Portney |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,847,802 A | 12/1998 | Menezes et al. |
| 5,864,378 A | 1/1999 | Portney |
| 5,876,442 A | 3/1999 | Lipshitz et al. |
| 5,898,473 A | 4/1999 | Seidner et al. |
| 5,929,969 A | 7/1999 | Roffman |
| 6,013,101 A | 1/2000 | Israel |
| 6,096,078 A | 8/2000 | McDonald |
| 6,110,202 A | 8/2000 | Barraquer et al. |
| 6,176,878 B1 | 1/2001 | Gwon et al. |
| 6,197,058 B1 | 3/2001 | Portney |
| 6,217,612 B1 | 4/2001 | Woods |
| 6,231,603 B1 | 5/2001 | Lang et al. |

FOREIGN PATENT DOCUMENTS

| | | |
|---|---|---|
| EP | 0337390 | 10/1989 |
| EP | 0342895 | 11/1989 |
| EP | 0351471 | 1/1990 |
| EP | 0480748 | 4/1992 |
| EP | 0488835 | 6/1992 |
| EP | 0566170 | 10/1993 |
| EP | 0691109 | 1/1996 |
| EP | 0780718 | 6/1997 |
| EP | 0897702 | 2/1999 |
| FR | 2666735 | 3/1992 |

| | | |
|---|---|---|
| FR | 0488835 | 6/1992 |
| GB | 939016 | 10/1963 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 91/09336 | 6/1991 |
| WO | 94/16648 | 8/1994 |
| WO | 95/03783 | 2/1995 |
| WO | 96/10968 | 4/1996 |
| WO | 96/15734 | 5/1996 |
| WO | 96/25126 | 8/1996 |
| WO | 97/12272 | 4/1997 |
| WO | 97/43984 | 11/1997 |
| WO | 98/21621 | 5/1998 |
| WO | 98/49594 | 11/1998 |
| WO | 98/56315 | 12/1998 |
| WO | 00/46629 | 8/2000 |
| WO | 00/66039 | 11/2000 |
| WO | 01/34067 | 5/2001 |
| ZA | 0888414 | 11/1988 |

OTHER PUBLICATIONS

Thornton, Color Atlas of Lens Implantation, Accommodation in Pseudophakia, pp. 159–162, 1991.
Amo Specs, Model AC–21B, 1992.
Chrion Vision, Nuvita MA20, 1997.
Menezo, et al. J Cataract Refract Surg 24, Aug. 1998.
Fechner, et al. J Cataract Refract Surg 24, Jan. 1998.

* cited by examiner

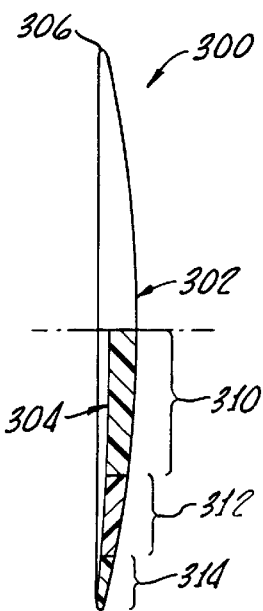
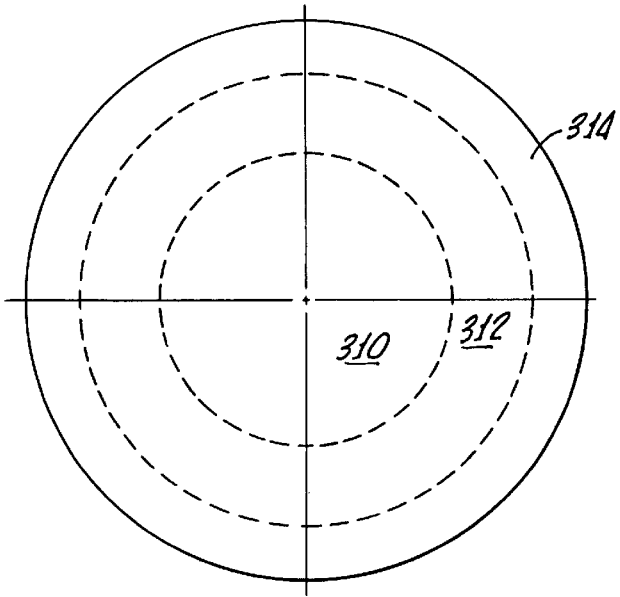
FIG. 8B.    FIG. 8A.
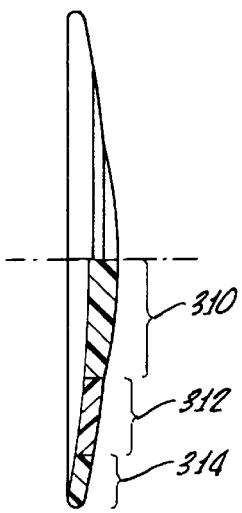
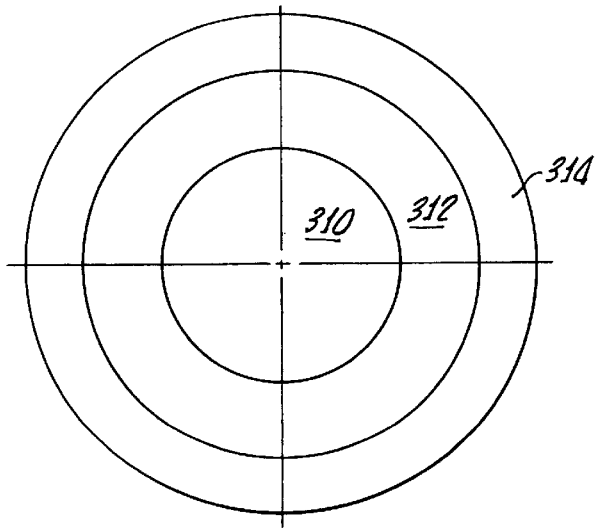
FIG. 9B.    FIG. 9A.

MONOFOCAL INTRAOCULAR LENS CONVERTIBLE TO MULTIFOCAL INTRAOCULAR LENS

BACKGROUND OF THE INVENTION

The present invention is related to intraocular lenses (IOLs). More particularly, the invention relates to such lenses which provide substantial advantages of both monofocal IOLs and multifocal IOLs.

Currently produced or conventional monofocal IOLs provide excellent optical quality for distance vision. Thus, such monofocal IOLs are produce with a single vision correction power, that being a vision correction power for distance or distance vision. However, such conventional monofocal IOLs do not provide sufficient near vision correction for reading or other situations where near vision is required.

One approach to providing near vision correction is currently in commercial use and is known generically as "multifocal IOLs". Such multifocal IOLs are produced with a plurality of optical powers, for example, a distance vision correction power and a near vision correction power. Although such lenses have proven to be quite effective in providing the desired range of vision correction power, they may not be totally acceptable to some patients due to the simultaneous vision characteristics of such lenses which may produce halo/glare phenomena.

An additional approach to providing the patient with a range of vision correction powers has been suggested and is commonly known as an "accommodating IOL". This type of IOL is designed to specifically provide both distance and vision correction powers. For example, the accommodating IOL may provide for the axial movement of a monofocal optic to vary the focus of an image on the retina. Such accommodating IOLs often are limited by the amount of movement required to produce adequate accommodation. For example, an accommodating IOL to be substantially effective should produce from 2.5 diopters to 3.5 diopters of add power to result in adequate near vision. There may not be adequate accommodative mechanisms remaining in the pseudo-phakic eye to move a monofocal lens the desired amount.

There continues to be a need to provide IOLs which are effective to provide both distance vision correction and near vision correction.

SUMMARY OF THE INVENTION

New IOLs have been discovered. The present IOLs take advantage of employing an optic adapted to have two different configurations to enhance the accommodation achievable in the eye in response to normal accommodative stimuli. Thus, the present IOLs have a first configuration in which the optic of the IOL has a monofocal distance vision correction power, for example, with the IOL in its resting state. In this first configuration, the present IOLs retain the excellent vision characteristics of a conventional monofocal distance vision correction IOL. However, the optics of the present IOLs are further adapted to have a second configuration to provide a plurality of different optical powers, for example, a near vision correction power in addition to a far or distance vision correction power.

Thus, the present lenses provide for vision correction or focusing for both near objects and far or distance objects. The negative aspects of simultaneous vision which occur with multifocal IOLs, such as night driving and the halo/glare phenomenon, are reduced, or even eliminated, with the present IOLs in the monofocal distance state or configuration. With the present IOL in the multifocal or second configuration, adequate near vision, for example, up to about 3.5 diopters in add power, are provided. The present IOLs are substantially not limited by the amount of accommodative ability remaining in the pseudo-phakic eye. The shape or configuration of the IOL is selectively changed for near vision by the patient during accommodation, for example, by the patient focusing from distance to near.

The present IOLs are relatively straightforward in construction and to manufacture or produce, can be implanted or inserted into the eye using systems and procedures which are well known in the art, and function effectively with little or no additional treatment or medications being required.

In one broad aspect of the present invention, IOLs for use in a mammalian eye are provided. Such IOLs comprise an optic adapted to focus light toward a retina of a mammalian, e.g., human, eye. The optics are further adapted to have a first configuration to provide a single optical power and a second configuration to provide a plurality of different optical powers. The optics advantageously are moveable between the first configuration and the second configuration. Preferably, the optics are moveable in cooperation with the mammalian eye between the first configuration and the second configuration. For example, the optic can be reshaped or is reshapable between the first configuration and the second configuration. Such reshaping preferably occurs in cooperation with the mammalian eye.

The present IOLs include means acting to at least assist in moving the optic into the second configuration, for example, in moving the optic between the first and second configuration. Such means can be, and preferably is, part of the optic of the present IOLs. Preferably, such means acts to do at least one of: facilitate the movement of the optic in cooperation with the mammalian eye, and inhibit the movement of the optic in cooperation with the mammalian eye. Thus, for example, the means can be provided as part of the optic to at least assist in controlling the reshaping or configuring of the optic between the first configuration and the second configuration.

In one embodiment, the optic has an outer surface and the means is located in proximity to the outer surface. For example, the outer surface may be part of an outer layer or portion substantially surrounding a core. The outer layer or portion can be specifically configured to provide a monofocal vision correction with the optic in the first configuration, such as with the optic in the rest position, and/or desired multifocal vision correction powers with the optic in the second configuration, such as with the optic being reshaped, for example, compressed, by the action of the mammalian eye.

The optic preferably includes at least one region adapted and positioned to do at least one of: facilitate the movement of the optic in cooperation with the mammalian eye, and inhibit the movement of the optic in cooperation with the mammalian eye. This at least one region preferably is located in proximity to the outer surface of the optic. For example, the at least one region may be in the form of an annulus or band around the optical axis of the optic. This region may have reduced thickness or rigidity or may be otherwise weakened so that the optic, under the influence of the mammalian eye, can move to a second configuration and provide a different optical power at that region. Alternately, or in addition, a region may be provided which has increased thickness or rigidity or may be otherwise strengthened so that even under the influence of the mammalian eye, the optic is inhibited, or even substantially prevented, from having a different optical power at the region.

Advantageously, the optic includes a plurality of such regions. Such region or regions may be part of the outer layer or portion of the optic or may be otherwise located at or near the outer surface of the optic.

In a very useful embodiment, the optic includes an inner core and an outer layer or portion adjacent to the inner core, preferably with the inner core being more deformable than the outer layer. In this embodiment, the outer layer or portion preferably is structured to do at least one of: facilitate the movement of the optic in cooperation with the movement of the mammalian eye, and inhibit the movement of the optic in cooperation with the mammalian eye, for example, in a manner as described elsewhere herein.

The present IOLs preferably are fabricated from one or more flexible, fully cured deformable polymeric materials. For example, an outer layer or portion may be provided that selectively deforms due to prescribed varied wall thicknesses or hinged areas. The outer portion or shell preferably encases or surrounds a core, preferably made of a more easily or readily deformable material, for example, a polymeric material which is more easily deformable relative to the polymeric material from which the outer layer or portion is made. The core preferably comprises a first polymeric material and the outer layer or portion comprises a different, second polymeric material. Although it is not necessary, it is preferred that the refractive indexes of the first and second polymeric materials be substantially the same, that is within about 7% or about 5% in refractive index of each other.

The optics of the present IOLs preferably comprise at least one polymeric material, and in a very useful embodiment at least two different polymeric materials. Overall, the optic preferably is sufficiently deformable to be inserted through a small incision into the eye. Upon contraction by the ciliary muscle due to accommodation, the optic is compressed or squeezed circumferentially. The optic is deformed or reshaped into a prescribed shape that results in a multifocal surface, preferably a multifocal anterior surface. This multifocal surface advantageously is a refractive surface that provides for near vision and preferably distance or far vision.

In one embodiment, the present IOLs in the second configuration provide only two optical powers, that is the present IOLs are bifocal in character, for example, providing for near vision correction in a central portion and distance vision radially outwardly of the central portion of the optic, such as near or along the periphery of the optic. Of course, the lenses can be produced so that the second configuration provides more than two optical powers, for example, a more elaborate multifocal surface, such as that described in Portney U.S. Pat. No. 5,225,858, the disclosure of which is incorporated in its entirety herein by reference.

In a particularly useful embodiment, the optic has an optical axis, and at least one of the plurality of different optical powers, in the second configuration, is provided in an annular region around the optical axis.

In one embodiment, the IOL further comprises a force transfer assembly secured to and extending radially outwardly from the optic. The force transfer assembly is adapted, when the IOL is located in the mammalian eye, to transfer a force exerted by the eye to the optic, thereby to facilitate the movement of the optic between the first configuration and the second configuration. Advantageously, the force transfer assembly includes an end extending from the optic adapted to contact a capsular bag of the mammalian eye when the IOL is located in the mammalian eye.

The reshaping or deformation of the optic from the first to the second configuration can cause an axial movement of the optic which has an additional effect on the accommodative power of the optic. The overall accommodative power of the optic in accordance with the present invention preferably is increased beyond the simple axial movement of a single configuration monofocal lens because of the first and second configurations of the present optics.

It should be noted that the force transfer assembly is not essential in accordance with the present invention. The optic can be sized and configured to fit within the capsular bag and to contact the capsular bag, in particular the periphery of the capsular bag, so that the force exerted on the capsular bag by the ciliary muscle can be transferred directly to the optic of the present IOL. Such IOLs in which the optics are sized and configured to contact the peripheral capsular bag are very effective in being reshaped to provide the desired vision correction power or powers. In addition, substantially filling the capsular bag volume with a deformable optic reduces the risk of decentration or tilt of the lens system in the eye, relative to lens systems in which the optic does not substantially fill the capsular bag volume. Providing for a reduced risk of decentration is highly advantageous, for example, as the capsular bag contracts. Even if the contraction of the capsular bag is asymmetric, for example, because the zonules are not of uniform strength, the elastic properties of the optic mitigate against this asymmetry and reduce the risk of decentration.

Substantially filling the capsular bag volume, as described above, may reduce the risk of posterior capsular opacification (PCO) particularly if the posterior surface of the optic remains in contact with the posterior wall of the capsular bag during all states of accommodation.

In a very useful embodiment, the present IOLs are deformable for insertion into the mammalian eye through a relatively small incision, for example, on the order of about 3.5 mm or less. Thus, the optic, and the force transfer assembly, if present, are deformable for insertion through a small incision into the eye. Such IOLs regain their original undeformed condition rapidly after being inserted into the mammalian eye. However, it is preferred that the entire IOL be sufficiently deformable to be passed through an incision in the eye which is less than the diameter of the IOL in its undeformed condition.

The present optics may be made of any suitable materials of construction. For example, the present optics may be made of one or more polymeric materials employing techniques used in manufacturing conventional polymeric material IOLs. Examples of the materials from which the present optics can be made include, without limitation, acrylic polymeric materials, silicone polymeric materials, and the like and combinations thereof. Although combinations of different polymeric materials may be employed, the present optics preferably are made of different polymeric materials of the same general chemical family. For example, the inner portion or core of the optic may be made of one silicone polymeric material while the outer portion or layer or other means is made of a different silicone polymeric material. Similarly, the core of the optic can be made of one acrylic polymeric material while the outer layer or other means is made of a different acrylic polymeric material. In any event, the present optics preferably are made of compatible materials of construction, that is materials which can be used to produce an effective IOL which remains as an intact structure in the eye without significant deterioration for periods of time extending for at least about 20 or about 25 years or more.

In one embodiment, the inner portion or core of the present optics is made of a very low modulus silicone polymeric material, while the outer portion or layer or other means is made of a higher strength silicone polymeric material. For instance, the outer portion may have a tensile yield strength of 625 psi, as measured using an SLJ-2 as a benchmark, and have a tensile modulus of elasticity at 150% elongation of 400 psi. To illustrate, the core of the optic can be composed of a silicone polymeric elastomer with the following material properties:

Optically clear;
Refractive index of at least about 1.40;
Shore A hardness of about 0; and
At least about 1000% elastic elongation.

The outer layer or other means of the present optics can be made of a different silicone elastomer with the following material properties:

Optically clear;
Refractive index of at least about 1.40;
Shore A hardness in a range of about 0 to about 45; and
An elastic elongation of at least about 150%, preferably in a range of about 150% to about 400%.

The outer layer or other means can be made of widely varying materials. Examples include, without limitation, rigid and foldable acrylic polymeric materials, rigid and foldable non-acrylic polymeric materials, deformable or foldable silicone polymeric materials and the like and combinations thereof. The outer layer or other portion can be hydrophobic or hydrophilic.

Many materials which meet the above-noted criteria are conventional and well known in the art. Therefore, a detailed description of such compositions is not presented here.

However, by way of illustration, the following materials of construction, based on constituent monomeric components, is presented.

TABLE

POTENTIAL FORMULATIONS

| Component | Core | Outer Layer or other Means |
|---|---|---|
| 2-phenylpropyl acrylate | 50% wt. | |
| 2-phenylpropyl methacrylate | | 70% wt. |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present optics are conveniently produced using conventional and well known techniques, such as molding techniques. In one embodiment, the outer layer or other means, for example, one or more annular bands of material, is produced in a separate mold and then placed into a mold into which is placed the monomeric or partially polymerized monomeric mixture of the core precursors. The combination is then heated to elevated temperatures, for example on the order of about 40° C. to about 100° C., and the combination is allowed to cure, preferably for about one hour to about 24 hours. The material in the mold is then post-cured, preferably at a temperature in the range of about 70° C. to about 130° C., for a period of time, preferably for about two hours to about 30 hours. After curing (and post-curing), the mold is disassembled and the molded optic recovered.

The force transfer assembly, if present, can be made or provided separately and then coupled to the optic or lens body, for example, in a mold in which the optic is cured or post-cured. Alternately, the force transfer assembly can be coupled to the lens body after the lens body is formed. Conventional techniques can be employed. For example, one or more recesses can be formed in the optic and the force transfer assembly can be secured to the optic by having an end placed in the recess, for example, in much the same manner in which a haptic or fixation member is secured to the optic of a conventional IOL.

Any suitable material or combination of materials of construction may be utilized in the force transfer assembly and the force transfer assembly can have any suitable configuration provided that such assembly is effective to at least partially transfer the force of the eye to the optic of the IOL. The force transfer assembly preferably is more rigid or less flexible than the core of the optic. However, the force transfer assembly preferably is sufficiently deformable to be folded or otherwise deformed to pass through a small incision for insertion into the eye. The force transfer assembly can be a single member substantially surrounding the optic, or can be a plurality, for example, about 2 or about 3 to about 4 or about 6, individual elements positioned around the peripheral edge of the optic. Although the force transfer assembly can include at least one hinge to facilitate axial movement of the optic in response to the action of the eye, preferably the force transfer assembly does not include a hinge.

The force transfer assembly preferably is made of a material or materials which are compatible with the eye and with the other material or materials included in the IOL. Examples of materials which can be included in the present force transfer assemblies include, but are not limited to, polypropylene, silicone polymeric materials, acrylic polymeric materials including but not limited to polymethylmethacrylate (PMMA), polyamides and the like and combinations thereof.

In a further broad aspect of the present invention, methods for inserting an IOL in an eye are provided. Such methods comprise providing an IOL in accordance with the present invention, as described herein. The IOL is placed into the eye, for example in the capsular bag of the eye, using equipment and techniques which are conventional and well known in the art. The IOL is placed in the eye so that the eye effectively cooperates with the IOL to provide accommodation as desired. After the IOL is inserted into the eye, any incision in the eye is closed. After a relatively short period of recuperation, the IOL provides the wearer of the IOL with substantially effective accommodation. No further treatments or medications, for example, to paralyze the ciliary muscle, to facilitate fibrosis or otherwise influence the position of the IOL in the eye, are required. Preferably the optic is deformed prior to being placed into the eye. Once the IOL is placed in the eye, and after a normal period of recovery from the surgical procedure, the IOL, in cooperation with the eye, provides the mammal or human wearing the IOL with the desired accommodation.

Any and all features described herein and combinations of such features are included within the scope of the present invention provided that the features of any such combination are not mutually inconsistent.

Additional aspects and advantages of the present invention are set forth in the following detailed description and claims, particularly when considered in conjunction with the

BRIEF DESCRIPTION OF THE DRAWINGS

FIGS. 8A and 8B are plan and side (partly in section) elevational views of an alternative IOL of the present invention in a rest, monofocal position; and FIGS. 9A and 9B are plan and side (partly in section) elevational views of the IOL of FIGS. 8A and 8B in a compressed, multifocal position.

DETAILED DESCRIPTION OF THE DRAWINGS

Figure 1:
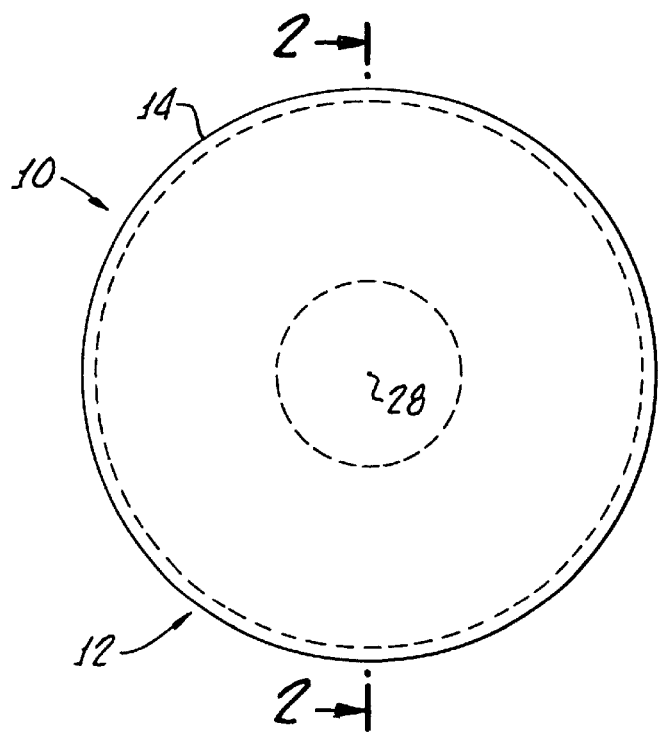
FIG. 1 is a front elevation view, with hidden lines, of an IOL in accordance with the present invention in a rest position.

Referring now to FIGS. 1, 2, 3 and 4, an IOL according to the present invention, shown generally at 10, includes a lens body or optic 12. This optic 12 includes a combination of components, that is, outer portion 14 and core portion 16. Outer portion 14 completely surrounds core portion 16 which is secured to the outer portion.

The core lens portion 16 is made of an optically clear material and is relatively highly deformable. Thus, not only is the core lens portion 16 sufficiently deformable so as to be foldable or otherwise deformable for insertion into the eye through a small incision, that is an incision in the eye smaller than the maximum, undeformed diameter of the optic 12, but, in addition, is sufficiently deformable to facilitate the movement of the optic 12 between a first configuration and a second configuration, as described elsewhere herein. The outer lens portion 14 preferably is more rigid than is the core lens portion 16.

The outer lens portion 14 is comprised of an optically clear material that is easily deformable when subjected to compression within the mammalian eye, and is sufficiently deformable for insertion into the eye through a small incision. In addition, the outer lens portion 14 is structured to be selectively deformable in response to a force exerted by the eye in which the IOL 10 is placed, for example, the contraction or contractive force, exerted by the ciliary muscle of the eye. The core lens portion 16 has a refractive index within about 5–7% of the refractive index of the outer lens portion 14 of optic 12.

The outer lens portion 14 and the inner lens portion 16 preferably are comprised of materials from the same basic chemical family. For example, the core lens portion 16 may be comprised of low or very low modulus silicone polymeric material having an index of refraction of at least about 1.40 or about 1.42, while the outer lens portion 14 can be comprised of a higher modulus silicone polymeric material having an index of refraction of at least about 1.42 or about 1.44 or about 1.46 or about 1.48 or higher. The tensile modulus of the silicone polymeric material making up the core lens portion 16 is, for example, no greater than about 20 psi to 50 psi at an elongation of 200%.

Alternately, the outer lens portion and the core lens portion 16 can be comprised of acrylic polymeric materials. In this embodiment, the core lens portion has a refractive index of at least about 1.42 or about 1.45.

One example of the materials used to produce the outer lens portion 14 and the inner lens portion 16 are as follows:

TABLE

POTENTIAL FORMULATIONS

| Component | Inner Portion | Outer Portion |
| --- | --- | --- |
| 2-phenylpropyl acrylate 2-phenylpropyl methacrylate | 50% wt. | 70% wt. |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present IOL 10 can be produced using conventional polymer processing techniques. For example, the present outer lens portion 14 can be produced separately using conventional molding, for example, injection or insert molding techniques. This outer lens portion 14 can then be used to produce optic 12 using conventional molding techniques, for example, injection molding techniques, together with the material used to produce the core lens portion 16.

The optical powers of the lens portions 14 and 16 may be controlled so as to satisfactorily address the needs of the patient in whose eye IOL 10 is inserted. Each of the lens portions 14 and 16 can have a suitable optical power.

The optical power of the optic 12 is a combination of the optical powers of the individual lens portions 14 and 16, and can be varied based on the individual optical powers of the portions 14 and 16 and the degree of reshaping and/or axial movement of the optic 12.

Figure 2:
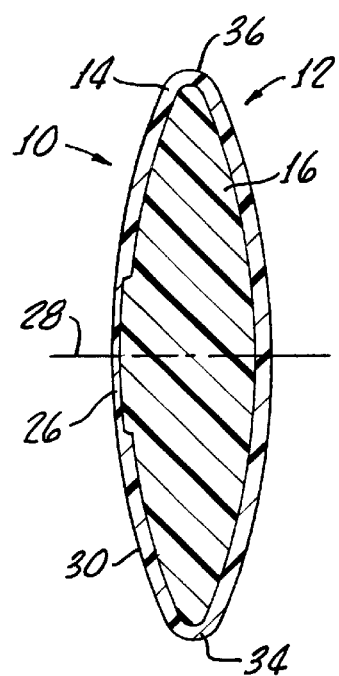
FIG. 2 is a cross-sectional view taken generally along line 2—2 of FIG. 1.

There are a number of ways to cause reshaping and/or axial movement of the optic 12. FIG. 2 illustrates an outer lens portion 14 structured to include a center section 26 of reduced thickness. The center section 26 surrounds the optical axis 28 of the optic 12 and is located on or near the anterior face 30 thereof. When the IOL 10, and in particular optic 12, is compressed, for example by squeezing peripheral regions 34 and 36 together, the optic is reshaped by an outward bowing of the anterior face 30. This squeezing is generally similar to the compressive force applied to the optic 12 by the eye in which the IOL 10 is placed. The outward bowing or reshaping is especially pronounced at region 37, because the reduced thickness section 26 is relatively more prone to give way from the internal pressure of the core lens portion 16. The core lens portion 16 thus extends forward, as seen for example in the central region 37 in FIG. 3, which is a slightly different embodiment than in FIG. 2.

The extended central region 37 of optic 10 provides near vision correction power. The remainder of the outer portion 14, having a thickness greater than section 26, is more resistant to reshaping under such compression than is section 26. Therefore, under such compression, the annular region 38 of optic 10 extending radially outward of center section 37 continues to provide distance vision correction power. Thus, the regions 37 and 38 of optic 10, under compression, provide both near and distance vision correction powers, respectively. In other words, the anterior surface 30 of optic 10 is a multifocal surface with the optic under compression. In contrast, with the optic 10 in the rest position as in FIG. 2, the anterior surface 30 is a monofocal surface.

Figure 3:
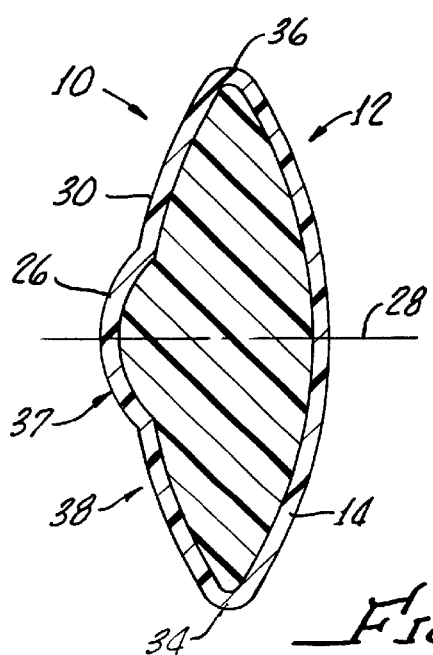
FIG. 3 is a cross-sectional view of the IOL shown in FIG. 1 in the multifocal configuration.

FIG. 3 illustrates an alternative embodiment of the IOL of the present invention which is substantially the same as that shown in FIG. 2, except for a different construction of the outer portion 14. Specifically, the center section 26 is made of a material that is relatively more susceptible to outward bowing than is the peripheral region surrounding it. The center section 26 may be injection molded in combination with the peripheral regions surrounding it to provide a relatively seamless and uninterrupted anterior face 30, at least in the rest position of the IOL. When the peripheral regions 34 and 36 are squeezed together the core lens portion 16 is placed in compression thus forcing the center section 26 in the anterior direction as shown in the extended region 37. Desirably, the material of the outer portion 14 is generally consistent, though the center section 26 has a different stiffness or elasticity that causes it to bow outward farther than the surrounding region.

The extent to which central region 37 extends forwardly, and therefore the magnitude of the near vision correction power obtainable by IOL 10, depends on a number of factors, such as the thickness of region 26, the overall structure of the outer portion 14 and/or the inner portion 16, the material of construction of the outer portion and/or the inner portion, the amount of force that the eye in which IOL 10 is placed can exert on the IOL and the like factors. The amount or degree of near power correction obtainable from IOL 10 can be controlled, or at least partially controlled, by varying one or more of these factors.

The IOL 10 is sized to fit within the capsular bag 50 of the eye 40 so as to be reshapable in response to the action of the ciliary muscle 46 and zonules 48 on the capsular bag of the eye. The IOL 10 should be sized to facilitate the movement and reshaping of the optic 12 in response to the action of the ciliary muscle 46 and zonules 48. For example, if the optic 12 is too large, the ciliary muscle 46 and zonules 48 will be inhibited from effectively contracting/relaxing so that the amount of movement and reshaping will be unduly restricted. Of course, if the IOL 10 is too small, the optic 12 will be ineffective to focus light on the retina of the eye 40, may cause glare and/or may not cooperate with the eye to effect the desired amount of accommodating movement/reshaping. If the IOL 10 is to be included in an adult human eye, the optic 10 preferably has a diameter in the range of about 8 mm to amount 12 mm.

The IOL 10 can be inserted into the capsular bag 50 of the eye 40 using conventional equipment and techniques, for example, after the natural crystalline lens of the eye is removed, for example, using a phaceomulsification technique.

Figure 4:
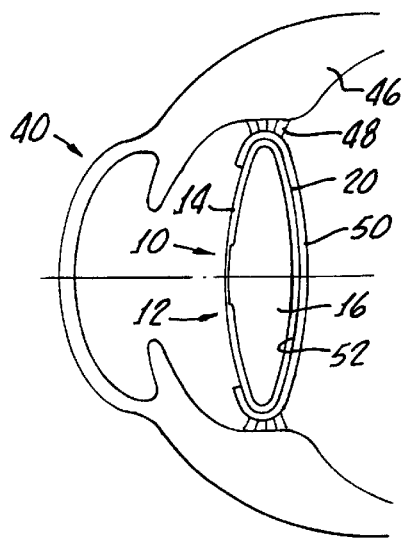
FIG. 4 is a fragmentary sectional view of an eye in which the IOL of FIG. 1 has been implanted, with the ciliary muscle of the eye in the relaxed state.

The IOL 10 in the eye 40, as shown in FIG. 4, is located so that the posterior face 20 of the outer lens portion 14 is in contact with the inner posterior wall 52 of the capsular bag 50. This contact is substantially maintained regardless of the configuration of the optic 12 in the eye 40. Such contact is effective in maintaining the structural integrity of the capsular bag 50 and, in addition, effectively inhibits the growth of cells from the capsular bag onto the optic, thereby at least inhibiting or reducing the severity of posterior capsular bag opacification (PCO).

The zonules 48 and the ciliary muscle 46 of the eye 40 are effective to move the capsular bag 50, thereby reshaping and moving the IOL 10. Thus, with the ciliary muscle being fully relaxed, the optic 12 is in a relatively flat configuration. Such configuration of optic 12 provides effective monofocal distance vision to the eye 40. This configuration is at least generally illustrated in FIGS. 2 and 4. With IOL 10 in the position as shown in FIG. 4, far away or distant objects are brought into focus. In this position, IOL functions much like a conventional monofocal IOL.

If a near object is to be viewed, the ciliary muscle 46 contracts or constricts causing the zonules 48 to relax tension on the capsular bag 50 and the IOL 10 included therein. IOL 10 is reshaped into a second configuration, illustrated generally in FIG. 3. This action of the ciliary muscle 46 and zonules 48 causes a reshaping of the optic 12 so that central anterior region 37 becomes apparent. This region 37 surrounds the optical axis 28 and provides near vision correction. The annular region 38 radially outwardly of region 37 continues to be configured for distance vision correction. In effect, the configuration of optic 12 illustrated in FIG. 3 is a multifocal configuration since both near vision correction and distance vision correction are present. When the ciliary muscle 46 again relaxes, the IOL 10 returns to the first configuration, shown generally in FIG. 2.

Thus, the present IOL 10 has the ability, in cooperation with the eye, to be reshaped to provide for both distance focus and near focus, and to be returned to its first configuration in which only distance focus is provided.

IOL 10, and in particular optic 12, is such that the amount of accommodation achievable at region 60 preferably is in the range of about 1 to about 4 or about 5 or about 6 diopters.

Figure 5:
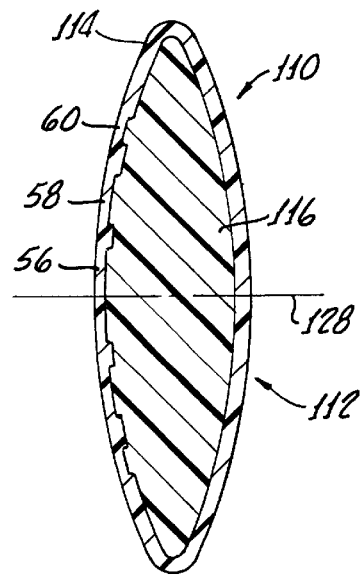
FIG. 5 is a cross-sectional view of an alternate IOL in accordance with the present invention.

FIG. 5 illustrates an alternate IOL, shown generally at 110, in accordance with the present invention. Except as expressly described herein, alternate IOL 110 is structured and functions similarly to IOL 10. Components of IOL 110 which correspond to components of IOL 10 are indicated by the same reference numerals increased by 100.

The primary difference between IOL 110 and IOL 10 relates to the structure of outer portion 114 of optic 112. Specifically, whereas outer portion 14 has only a single region 26 of reduced thickness, outer portion 114 has three regions 56, 58 and 60 of reduced thickness. The central region 56 surrounds the optical axis 128 and has a variable thickness. Region 58 is an annular region located outwardly of region 56 and annular region 60 is located outwardly of region 56 and is reduced in radial dimension relative to region 56.

Under compressive force from the eye in which IOL 110 is placed, the inner portion 116 forces the regions 56, 58 and 60 to extend outwardly. The variable thickness of region 56 leads to a central region of the compressed optic 112 having an intermediate (between near and far) vision correction power. The reduced thicknesses of outer regions 58 and 60 lead to two regions of the compressed optic 112 having near vision correction powers. In general, the multifocal anterior surface of compressed optic 112 has more varied optical powers than does the multifocal anterior surface of compressed optic 12. The optical power curve of compressed optic 112 may resemble, at least in general, a power curve disclosed in the above-noted Portney U.S. Patent which is incorporated herein by reference. Such a varied multifocal configuration provides the wearer of IOL 110 with enhanced vision over a wider range of distances.

Figure 6:
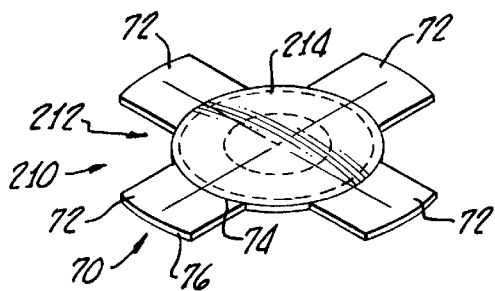
FIG. 6 is a top side view, in perspective, of an additional IOL in accordance with the present invention.
Figure 7:
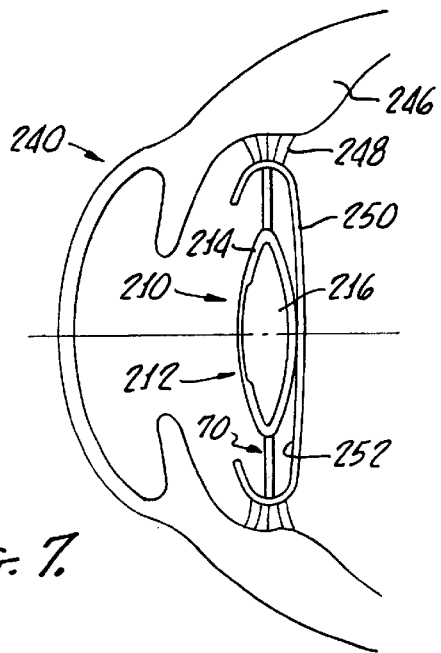
FIG. 7 is a fragmentary sectional view of an eye in which the additional IOL of FIG. 6 has been implanted, with the ciliary muscle of the eye in the relaxed state.

FIGS. 6 and 7 illustrate an additional IOL, shown generally at 210, in accordance with the present invention. Except as expressly described herein, additional IOL 210 is structured and functions similarly to IOL 10. Components of IOL 210 which correspond to components of IOL 10 are indicated by the same reference numerals increased by 200.

The primary difference between IOL 210 and IOL 10 relates to the presence in IOL 210 of a force transfer assembly, shown generally at 70. In particular, as best shown in FIG. 6, force transfer assembly 70 includes four identically structured transfer members 72 which extend radially outwardly from the proximal end 74, which is attached to optic 212, to an outer or distal end 76. Each of the transfer members 72 has a substantially flat configuration and is made of an acrylic polymeric material which is deformable for insertion of the IOL 210 into the eye, yet is more rigid than the outer lens portion 214 to facilitate the transfer of force from the eye 240 to the optic 212. One particularly useful acrylic polymeric material for use as a material of construction of the members 72 is a polymeric composition produced from the following mixture of monomers:

Ethyl acrylate 57.1% by weight
Ethyl methacrylate 27.7% by weight
Trifluoroethyl
 methacrylate 9.82% by weight
Ethylene glycol dimethacrylate 3.75% by weight
UV chromophore 1.5% by weight
Initiator (thermal) 0.13% by weight The IOL 210 can be produced by molding the outer lens portion 214, and transfer members 72 separately and then molding can be employed to form the combination of the inner lens portion 216, the transfer members and the outer lens portion 214.

With the force transfer assembly 70 in place, if the IOL 210 is to be included in an adult human eye, the optic 212 preferably has a diameter in the range of about 3.5 mm to about 7 mm, and the IOL 210 has an overall maximum diameter, including the force transfer assembly 70 in the rest state, that is fully extended from the optic 212, in the range of about 8 mm to about 12 mm.

Insertion can be accomplished using conventional techniques, for example, after the natural lens of the eye has been removed.

In the eye, IOL 210 moves axially in response to the action of the ciliary muscle 246 and zonules 248 through the force transfer assembly 70. In addition, the optic 212 is reshaped in response to the action of the ciliary muscle 246 and zonules 248 through force transfer assembly 70. The posterior face 80 of outer lens portion 214 remains in substantial contact with the inner posterior wall 252 of the capsular bag 250. Such contact occurs whether the IOL is located in its posterior most position in eye 240 or in its anterior most position in eye 240. Such contact inhibits the growth of cells from the capsular bag 250 onto optic 210 and inhibits PCO.

IOL 210 provides focus accommodation because of the reshaping of the optic 212, in much the same way as when optic 12 is reshaped. However, optic 212 provides further accommodation because of the axial movement of optic 212. Thus, optic 212 may provide additional or enhanced accommodation relative to optic 12.

An alternative embodiment of a convertible IOL 300 the present invention is illustrated at rest in FIGS. 8A–8B, and after having been compressed into a multifocal lens in FIGS. 9A–9B. The IOL 300 has a generally convex anterior face 302, a concave posterior face 304, and a surrounding peripheral edge 306. A plurality of differing concentric regions enable the IOL 300 to be converted between a monofocal lens and a multifocal lens. With reference to FIG. 8A, the IOL 300 includes a circular center section 310, an intermediate section 312 surrounding the circular center section, and an outer peripheral section 314. Desirably, the three sections 310, 312, and 314 are concentrically disposed and contiguous, although other configurations are possible. The three sections are also shown in cross-section in the lower portion of FIG. 8B.

In a preferred embodiment, the three sections 310, 312, and 314 possess different rigidity or softness characteristics to cause them to bend or bow in the anterior direction at different rates when under radial compressive stresses. For example, the intermediate section 312 may be relatively harder than either the center section 310 or outer peripheral section 314, and thus be less susceptible to forward bowing. This configuration is seen in FIGS. 9A and 9B where the center section 310 and the outer peripheral section 314 exhibit more pronounced curvatures than the intermediate section 312. In this way, the center section 310 provides near vision, while the intermediate section 312 and outer peripheral section 314 provide varying degrees of far vision correction. The three sections 310, 312, and 314 may be injection molded to provide a relatively seamless and uninterrupted anterior face 302, at least in the rest position of the IOL 300.

The present invention provides accommodating IOLs which cooperate with the eye to achieve advantageous amounts, preferably enhanced amounts, of accommodation. Such accommodation, as described herein, is often increased, for example relative to previous monofocal accommodating IOLs. In addition, halo/glare phenomena are reduced, for example, relative to previous multifocal IOLs.

While this invention has been described with respect to various specific examples and embodiments, it is to be understood that the invention is not limited thereto and that it can be variously practiced within the scope of the following claims.

What is claimed is:

1. An intraocular lens for use in a mammalian eye comprising:
 an optic structured to focus light toward a retina of the mammalian eye and being further structured to have a first configuration to provide a single optical power and a second configuration to provide a plurality of different optical powers, wherein the optic, when the intraocular lens is in use in a mammalian eye, is movable in response to force applied to the optic by the mammalian eye between the first configuration and the second configuration.

2. The intraocular lens of claim 1 wherein the optic is reshapeable between the first configuration and the second configuration.

3. The intraocular lens of claim 1 wherein the second configuration provides only two optical powers.

4. The intraocular lens of claim 1 wherein the single optical power is an optical power for distance vision.

5. The intraocular lens of claim 1 wherein at least one of the plurality of different optical powers is an optical power for near vision.

6. The intraocular lens of claim 5 wherein at least one of the plurality of different optical powers is an optical power for distance vision.

7. The intraocular lens of claim 1 wherein the optic has an optical axis and at least one of the plurality of different optical powers is provided in an annular region around the optical axis.

8. The intraocular lens of claim 1 wherein the optic comprises at least one polymeric material.

9. The intraocular lens of claim 1 wherein the optic is sufficiently deformable to be inserted through a small incision into the mammalian eye.

10. The intraocular lens of claim 1 comprising means for at least assisting in forming the second configuration.

11. The intraocular lens of claim 10 wherein the means does at least one of: facilitate the movement of the optic in cooperation with the mammalian eye, and inhibit the movement of the optic in cooperation with the mammalian eye.

12. The intraocular lens of claim 10 wherein the optic has an outer surface and the means is located in proximity to the outer surface.

13. The intraocular lens of claim 1 wherein the optic includes at least one region adapted and positioned to do at least one of: facilitate the movement of the optic in cooperation with the mammalian eye, and inhibit the movement of the optic in cooperation with the mammalian eye.

14. The intraocular lens of claim 13 wherein the optic has an outer surface and the region is located in proximity to the outer surface.

15. The intraocular lens of claim 13 wherein the optic has an optical axis and the at least one region is in the form of an annulus around the optical axis.

16. The intraocular lens of claim 13 wherein the optic includes a plurality of the regions.

17. The intraocular lens of claim 1 wherein the optic includes an inner core and an outer layer adjacent the inner core.

18. The intraocular lens of claim 17 wherein the outer layer substantially surrounds the inner core.

19. The intraocular lens of claim 17 wherein the inner core is more deformable than the outer layer.

20. The intraocular lens of claim 17 wherein the outer layer is structured to do at least one of: facilitate the movement of the optic in cooperation with the mammalian eye, and inhibit the movement of the optic in cooperation with the mammalian eye.

21. The intraocular lens of claim 17 wherein the outer layer has sections of varying stiffness to cause varied forward bowing of the lens and the plurality of different optical powers upon being subjected to radially compressive forces from the eye.

22. The intraocular lens of claim 21 wherein the outer layer has a center section and at least one section outside of the center section that is stiffer than the center section.

23. The intraocular lens of claim 17 wherein the inner core comprises a first polymeric material and the outer layer comprises a different, second polymeric material.

24. The intraocular lens of claim 1 wherein the second configuration provides more than two optical powers.

25. The intraocular lens of claim 1 wherein the lens includes a center section, an intermediate section adjacent the center section that is stiffer than the center section, and an outer section adjacent and outside the intermediate section that is less stiff than the intermediate section, to cause varied forward bowing of the lens and a pluraality of different optical powers upon being subjected to radially compressive forces from the eye.

26. The intraocular lens of claim 1 which further comprises a force transfer assembly secured to and extending radially outwardly from the optic, the force transfer assembly being adapted, when the intraocular lens is located in the mammalian eye, to transfer a force exerted by the eye to the optic, thereby to facilitate the movement of the optic between the first configuration and the second configuration.

27. The intraocular lens of claim 26 wherein the force transfer assembly includes an end extending away from the optic adapted to contact a capsular bag of the mammalian eye when the intraocular lens is located in the mammalian eye.

28. An intraocular lens for use in a mammalian eye comprising:
an optic structured to focus light toward a retina of the mammalian eye, the optic including a surface that is deformable from a first configuration providing the optic with a single optical power to a second configuration providing the optic with a plurality of different optical powers, wherein the surface, when the intraocular lens is in use in a mammalian eye, is resiliently deformable between the first configuration and the second configuration in response to force applied to the optic by the mammalian eye.

* * * * *